United States Patent
Myung et al.

(10) Patent No.: US 9,706,918 B2
(45) Date of Patent: Jul. 18, 2017

(54) MODULAR LENS ADAPTERS FOR MOBILE ANTERIOR AND POSTERIOR SEGMENT OPHTHALMOSCOPY

(71) Applicant: The Board of Trustees of the Leland Stanford Junior University, Stanford, CA (US)

(72) Inventors: David Myung, Santa Clara, CA (US); Robert Tienhan Chang, Palo Alto, CA (US); Lingmin He, Palo Alto, CA (US); Alex Nugent, Santa Clara, CA (US); Huynh P. Van, Garden Grove, CA (US); Ira G. Wong, San Mateo, CA (US); Alexandre Jais, Stanford, CA (US); Mark Blumenkranz, Los Altos Hills, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 14/893,951

(22) PCT Filed: May 30, 2014

(86) PCT No.: PCT/US2014/040203
§ 371 (c)(1),
(2) Date: Nov. 25, 2015

(87) PCT Pub. No.: WO2014/194182
PCT Pub. Date: Dec. 4, 2014

(65) Prior Publication Data
US 2016/0113489 A1    Apr. 28, 2016

Related U.S. Application Data

(60) Provisional application No. 61/829,548, filed on May 31, 2013, provisional application No. 61/896,011, filed on Oct. 25, 2013.

(51) Int. Cl.
*A61B 3/14* (2006.01)
*A61B 3/10* (2006.01)
(Continued)

(52) U.S. Cl.
CPC .............. *A61B 3/1208* (2013.01); *A61B 3/10* (2013.01); *A61B 3/117* (2013.01); *A61B 3/125* (2013.01);
(Continued)

(58) Field of Classification Search
USPC .................................................. 351/206, 221
See application file for complete search history.

(56) References Cited

U.S. PATENT DOCUMENTS

| 4,461,551 A | 7/1984 | Blaha |
| 4,586,892 A | 5/1986 | Ichizawa et al. |

(Continued)

FOREIGN PATENT DOCUMENTS

| CN | 103110401 A | 5/2013 |
| JP | 2008295725 A | 12/2008 |

(Continued)

OTHER PUBLICATIONS

Bastawrous; Smartphone fundoscopy; Ophthalmology; 119(2); pp. 432-433.e2; Feb. 2012.
(Continued)

*Primary Examiner* — Jack Dinh
(74) *Attorney, Agent, or Firm* — Shay Glenn LLP (57) ABSTRACT

A modular lens adapter system or kit is provided for mobile anterior and posterior segment ophthalmoscopy. Equipped with various lens adapter modules, respective lenses and a mobile imaging device, a user is provided with tools for various mobile ophthalmoscopy imaging applications. Eye care practitioners can use their existing lenses to customize the modular lens adapter system in a cost-effective way, (Continued)

which allows for mobile and remote capture, viewing, and utilization of clinical images. The various modules are also adaptable to nearly any type of phone or tablet regardless of its dimensions or presence of a protective case. The invention also addresses the need for fewer, smaller, less expensive, and easier to use ophthalmic imaging equipment, which is further important in enabling a broad base of users.

13 Claims, 10 Drawing Sheets

(51) Int. Cl.
| | |
|---|---|
| A61B 3/12 | (2006.01) |
| A61B 3/117 | (2006.01) |
| A61B 3/125 | (2006.01) |
| A61B 5/00 | (2006.01) |
| A61B 90/30 | (2016.01) |

(52) U.S. Cl.
CPC ............... *A61B 3/14* (2013.01); *A61B 3/145* (2013.01); *A61B 5/6898* (2013.01); *A61B 3/12* (2013.01); *A61B 2090/309* (2016.02); *A61B 2560/0443* (2013.01)

(56) References Cited

U.S. PATENT DOCUMENTS

| | | | |
|---|---|---|---|
| 4,856,892 | A | 8/1989 | Ben Tovim |
| 6,766,041 | B2 | 7/2004 | Golden et al. |
| 6,889,006 | B2 | 5/2005 | Kobayashi |
| 7,806,528 | B2 | 10/2010 | Bedell et al. |
| 7,883,210 | B2 | 2/2011 | Filar |
| 8,253,787 | B2 | 8/2012 | Yamamoto |
| 8,454,166 | B2 | 6/2013 | Fateh |
| 8,511,820 | B2 | 8/2013 | Trachtman |
| 8,725,210 | B2 | 5/2014 | Yang |
| 8,760,569 | B2 | 6/2014 | Yang |
| 8,798,453 | B2 | 8/2014 | Lawton |
| 8,836,778 | B2 | 9/2014 | Ignatovich et al. |
| 8,862,183 | B2 | 10/2014 | Kulas |
| D717,856 | S | 11/2014 | Slawson et al. |
| 8,888,288 | B2 | 11/2014 | Iravani et al. |
| 8,905,543 | B2 | 12/2014 | Davis |
| 8,922,366 | B1 | 12/2014 | Honoré et al. |
| 9,019,420 | B2 | 4/2015 | Hurst et al. |
| 9,031,610 | B2 | 5/2015 | Kulas |
| 9,066,683 | B2 | 6/2015 | Zhou |
| 9,149,179 | B2 | 10/2015 | Barnard et al. |
| 9,215,977 | B2 | 12/2015 | Bitran |
| 2004/0208343 | A1 | 10/2004 | Golden et al. |
| 2005/0270484 | A1 | 12/2005 | Maeda et al. |
| 2007/0280677 | A1 | 12/2007 | Drake et al. |
| 2009/0062686 | A1 | 3/2009 | Hyde et al. |
| 2010/0328420 | A1 | 12/2010 | Roman |
| 2011/0085138 | A1 | 4/2011 | Filar |
| 2011/0299036 | A1 | 12/2011 | Goldenholz |
| 2012/0176689 | A1 | 7/2012 | Brown |
| 2012/0229617 | A1 | 9/2012 | Yates et al. |
| 2012/0320340 | A1 | 12/2012 | Coleman |
| 2013/0083185 | A1 | 4/2013 | Coleman |
| 2013/0150123 | A1 | 6/2013 | Kulas |
| 2013/0293840 | A1 | 11/2013 | Bartels |
| 2013/0300919 | A1 | 11/2013 | Fletcher et al. |
| 2014/0002792 | A1 | 1/2014 | Filar |
| 2014/0071547 | A1 | 3/2014 | O'Neill et al. |
| 2014/0078594 | A1 | 3/2014 | Springer |
| 2014/0085603 | A1 | 3/2014 | Su et al. |
| 2014/0114208 | A1 | 4/2014 | Smith et al. |
| 2014/0132932 | A1 | 5/2014 | Jung |
| 2014/0228668 | A1 | 8/2014 | Wakizaka et al. |
| 2014/0268053 | A1 | 9/2014 | Fabian et al. |
| 2014/0327753 | A1 | 11/2014 | Prabhakar |
| 2014/0327754 | A1 | 11/2014 | Prabhakar |
| 2014/0327755 | A1 | 11/2014 | Prabhakar |
| 2014/0350379 | A1 | 11/2014 | Verdooner |
| 2015/0002950 | A1 | 1/2015 | O'Neill et al. |
| 2015/0045012 | A1 | 2/2015 | Siminou |
| 2015/0098060 | A1 | 4/2015 | Zhou |
| 2015/0103317 | A1 | 4/2015 | Goldfain et al. |
| 2015/0223678 | A1 | 8/2015 | Goldfain et al. |
| 2015/0223686 | A1 | 8/2015 | Wang |
| 2015/0254524 | A1 | 9/2015 | Dickrell et al. |
| 2015/0257639 | A1 | 9/2015 | Manquez Hatta et al. |
| 2015/0313462 | A1 | 11/2015 | Reis |

FOREIGN PATENT DOCUMENTS

| | | |
|---|---|---|
| WO | WO 03/043363 A1 | 5/2003 |
| WO | WO2012/176960 A1 | 12/2012 |
| WO | WO2014/181096 A1 | 11/2014 |
| WO | WO2015/035229 A2 | 3/2015 |
| WO | WO2015/054672 A1 | 4/2015 |

OTHER PUBLICATIONS

Chakrabarti; Application of mobile technology in ophthalmology to meet the demands of low-resource settings; Journal of Mobile Technology in Medicine; 1(4S); pp. 1-3; Dec. 2012.

Chhablani et al.; Smartphones in ophthalmology; Indian J. Ophthalmol.; 60(2); pp. 127-131; Mar./Apr. 2012 (Author Manuscript).

Haddock et al.; Simple, inexpensive technique for high-quality smartphone fundus photography in human and animal eyes; Journal of Ophthalmology; 2013; pp. 1-5; published online Sep. 19, 2013.

Hester et al.; Smart Phoneography—how to take slit lamp photographs with an iphone; 12 pages; retrieved Jul. 30, 2015 from the internet (http://eyewiki.aao.org/Smart_Phoneography_-_How_to_take_slit_lamp_photographs_with_an_iPhone).

Kim et al.; Smartphone photography safety; Ophthalmology; 119(10); pp. 220-2201; Oct. 2012.

Lord et al.; Novel uses of smartphones in ophthalmology; Ophthalmology; 117 (6); pp. 1274-1274 e3; Jun. 2010.

Teichman et al.; From iphone to eyephone: a technique for photodocumentation; Can. J. Ophthalmol.; 46(3); pp. 284-286; Jun. 2011.

Echanique et al.; Ocular Cellscope; University of California at Berkeley; Electrical engineering and computer sciences; 23 pages; retrieved from the internet (http://digitalassets.lib.berkeley.edu/techreports/ucb/text/EECS-2014-91.pdf); May 16, 2014.

Myung et al.; U.S. Appl. No. 15/186,266 entitled "Adapter for retinal imaging using a hand held computer," filed Jun. 17, 2016.

MODULAR LENS ADAPTERS FOR MOBILE ANTERIOR AND POSTERIOR SEGMENT OPHTHALMOSCOPY

FIELD OF THE INVENTION

This invention relates generally to ophthalmoscopy. In particular, the invention relates to lens adapters for mobile ophthalmoscopy that can be used in a modular fashion with mobile imaging devices, like smartphones.

BACKGROUND OF THE INVENTION

Over the past decade, ophthalmic imaging has moved rapidly from film to digital. However, most of today's gold standard digital fundus cameras, for example, are large, expensive tabletop medical devices only available in eye clinics. With the advent of the smartphone and ever improving built-in cameras rivaling point-and-shoot pocket digital cameras, eye care providers have the opportunity to capture high quality images anywhere using their existing lenses without the need for expensive equipment. Combined with ubiquitous fast wireless internet, cloud storage, smartphone-enabled electronic medical records, and encrypted messaging, a modern smartphone can now be instantly transformed into a low cost, portable, ophthalmic imaging camera. The present invention advances the art by providing a customizable adapter system or kit for mobile anterior and posterior segment ophthalmoscopy.

SUMMARY OF THE INVENTION

A modular lens adapter system or kit is provided for mobile anterior and posterior segment ophthalmoscopy. Equipped with various lens adapter modules, respective lenses and a mobile imaging device, a user is provided with tools for mobile ophthalmoscopy. The user can setup for various mobile ophthalmoscopy imaging applications like:
  Posterior segment ophthalmoscopy using the ophthalmoscopy lens adapter with the mobile imaging device and its internal (variable intensity) light source.
  Posterior segment ophthalmoscopy using the ophthalmoscopy lens adapter with the mobile imaging device and an external (variable intensity) light source.
  Posterior segment ophthalmoscopy using the ophthalmoscopy lens adapter with the mobile imaging device using the (variable intensity) light source of the macro lens adapter (without the macro lens mounted).
  Anterior segment ophthalmoscopy using the macro lens adapter and mounted a macro lens with the mobile imaging device optionally using the (variable intensity) light source of the macro lens adapter, where the ophthalmoscopy lens adapter is detached from the mobile imaging device.
  Anterior segment ophthalmoscopy using the macro lens adapter and mounted a macro lens with the mobile imaging device and its internal (variable intensity) light source, where the ophthalmoscopy lens adapter is detached from the mobile imaging device.
  Iridocorneal angle ophthalmoscopy (gonioscopy) using a modified macro lens adapter that allows mounting of a gonioscopy lens with the mobile imaging device optionally using the (variable intensity) light source of the macro lens adapter or the mobile device's internal flash.

With the embodiments of this invention, eye care practitioners can use their existing lenses to customize the modular lens adapter system in a cost-effective way, which allows for mobile and remote capture, viewing, and utilization of clinical images. The various modules are also adaptable to nearly any type of phone, tablet, or other mobile imaging device regardless of its dimensions or presence of a protective case. The embodiments also address the reduced need for extra ophthalmic equipment, which is further important in enabling a broad base of users.

BRIEF DESCRIPTION OF THE DRAWINGS

FIGS. 4-5 show exploded views of the mobile ophthalmoscopy system or kit according to exemplary embodiments of the invention.

FIGS. 6-9 show various views of the mobile ophthalmoscopy system or kit according to an exemplary embodiment of the invention with the mobile imaging device and its casing to which the ophthalmoscopy lens adapter 100 and macro lens adapter 200 are adapted. FIG. 6 is a top view.

FIGS. 10-13 show various views of the mobile ophthalmoscopy system or kit according to an exemplary embodiment of the invention with the mobile imaging device and its casing to which the ophthalmoscopy lens adapter 100 and macro lens adapter 300 are adapted. FIG. 10 is a top view.

FIGS. 14-15 show various views of the mobile ophthalmoscopy system or kit according to an exemplary embodiment of the invention with the mobile imaging device and its casing to which the ophthalmoscopy lens adapter 100 and macro lens adapter 200 are adapted. FIG. 15 is a side view. In both examples lens mount 120 has been folded (flush) with respect to the telescoping arm 110, which has been minimized in size by sliding segment 112 within segment 114. The sizing of the opening 126 of the lens mount 120 matches the diameter of the arm segment(s) 112, 114 of the telescoping arm 110.

DETAILED DESCRIPTION

In a first embodiment of the invention a modular lens adapter system or kit is provided for anterior and posterior segment ophthalmoscopy in a mobile fashion. In a second embodiment of the invention a modular lens adapter system or kit is provided for anterior, posterior, and iridocorneal angle segment ophthalmoscopy in a mobile fashion. Adapter modules for imaging each of the eye segments can be removable attached to a mobile imaging device as desired by the user making mobile ophthalmoscopy possible.

Examples of mobile imaging devices are phones, smartphones (e.g. iPhone), tablet computing devices (e.g. iPad), high definition webcam (but wired and wireless), as well as digital cameras and video cameras with wireless and/or Bluetooth connectivity, all with at least a camera option for making still images and/or video. The exemplary embodiments are portrayed with an iPhone and different adapter modules, although these embodiments are easily adapted to other smartphone brands and mobile devices as specified above.

Posterior Segment Adapter Module

Figure 1:
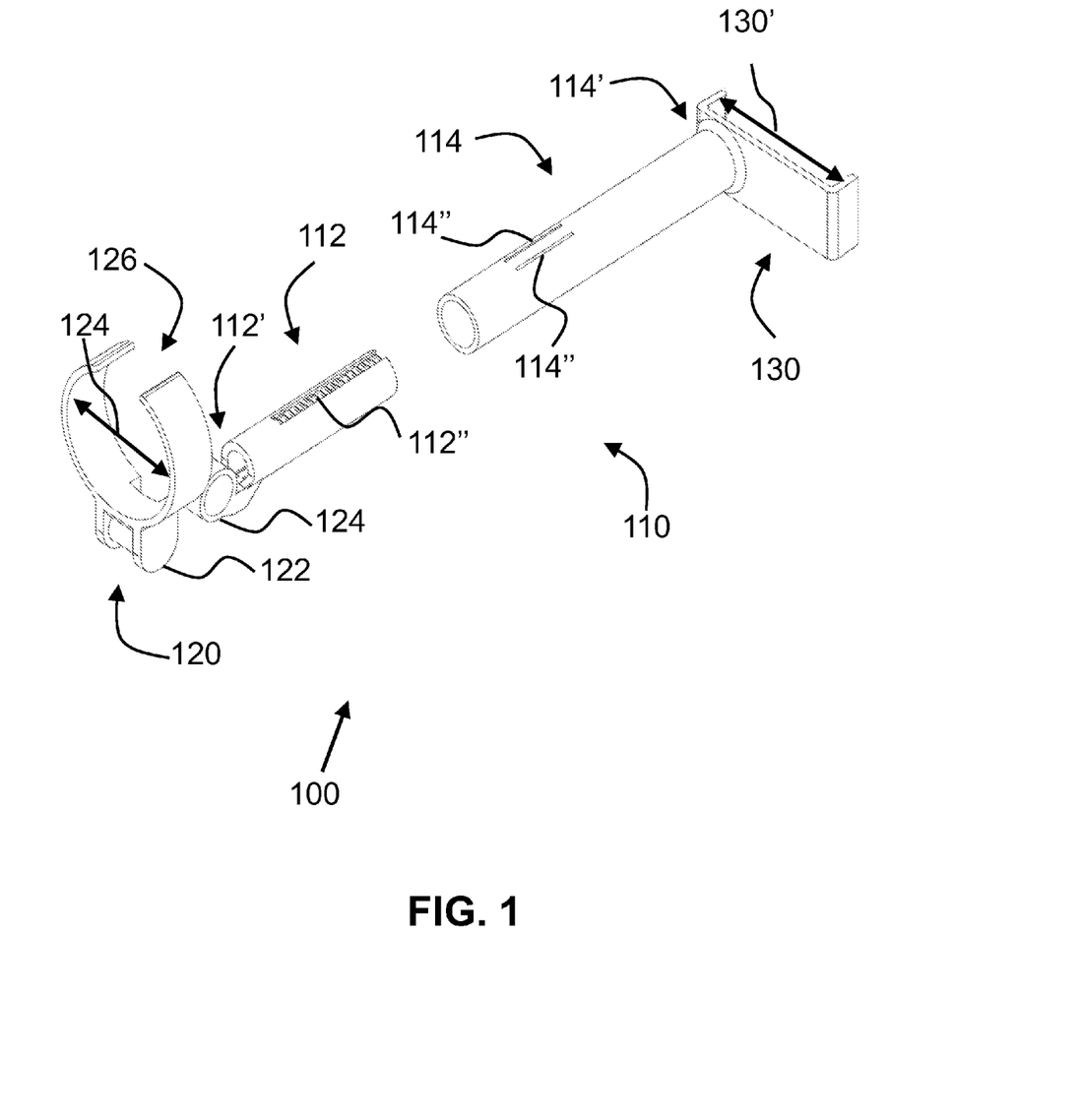
FIG. 1 shows an ophthalmoscopy lens adapter 100 according to an exemplary embodiment of the invention.

A first adapter module as shown in FIG. 1 is an ophthalmoscopy lens adapter 100, which can be used for imaging the posterior segment of an eye. In this example, the ophthalmoscopy lens adapter 100 has a telescoping arm 110 with two segments 112, 114, where segment 112 can slide within the shaft of segment 114. In another embodiment, there are three or more telescoping segments that enable the adapter to collapse to a smaller size and extend to a broader range of lengths. In yet another embodiment, there is only one segment, which is not telescopic and at a fixed length.

The slideable shaft allows for adjustment of the working distance (adjusting the focal point) between the mobile imaging device and an ophthalmoscopy lens mounted to ophthalmoscopy lens adapter 100 via lens mount 120. The telescoping arm 110 can vary the working distance of lens mount 120 (i.e. the mounted ophthalmoscopy lens) relative to the mobile phone mount 130 in a range of 1 cm to 20 cm. To assist in maintaining and/or guiding of a desired working position of segment 112 with respect to segment 114, an array with bumps 112" can be fabricated along the top surface of segment 112. Inside the shaft of segment 114, facing toward the bumps 112" one or more bumps (not shown), with similar dimension as the bumps in array 112", could be positioned such that they would line up with bumps 112" and provide relatively more friction to assist in the maintenance of the desired working distance of the telescoping arm 110. The one or more bumps within segment 114 could be positioned anywhere inside the segment wall of segment 114. In a preferred embodiment, the one or more bumps could be positioned on the inner wall of the rectangular portion that is created by slits 114". The rectangular portion facilitates easier sliding of the shafts as it decreases the friction between the bumps of segment 112 and 114 due to the fact that the rectangular portion would slightly bend outward with respect to its segment.

A telescoping arm like 110 is one of the various possible mechanisms to adjust the working distance, as a skilled artisan would appreciate. Various other mechanisms could also work, such as folding or collapsing arm segments with joints and therefore the invention is not limited to telescoping segments. The objective of the telescopic arms or even the folding or collapsing arm segments is that the size can be minimized for easy storage. In one example with the same objective of minimizing space, the telescoping arms could also be separated from each other.

Telescoping arm 110 has two ends: one end 112' for segment 112 and the other end 114' for segment 114. At end 112' lens mount 120 is attached. In the example of FIG. 1, lens mount 120 is adapted or movably fixed to segment 112 by means of a joint or hinge mechanism, which is made up by joint/hinge parts 122 and 124. The joint mechanism allows lens mount 120 to be rotated in different positions with respect to segment 112.

Figure 14:
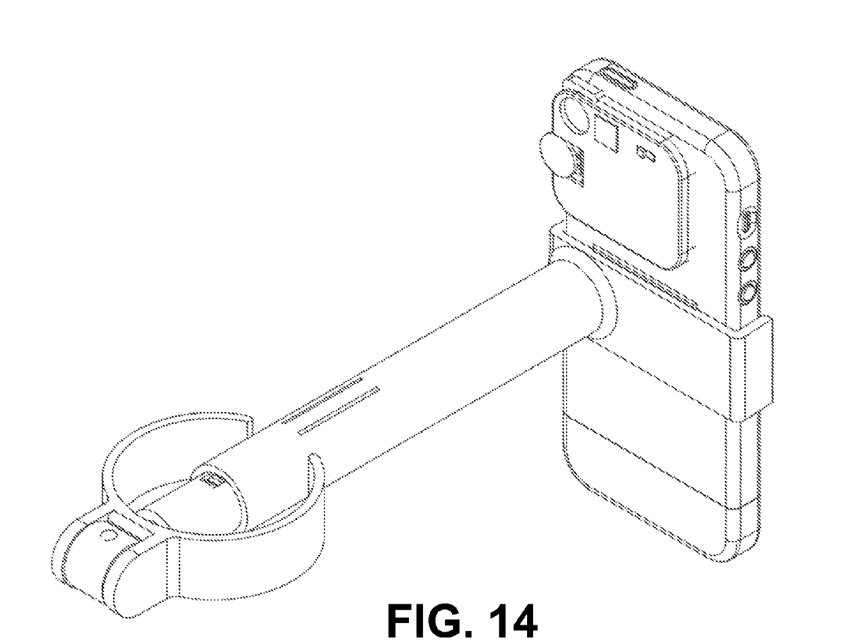
FIG. 14 is a three-dimensional view.
Figure 15:
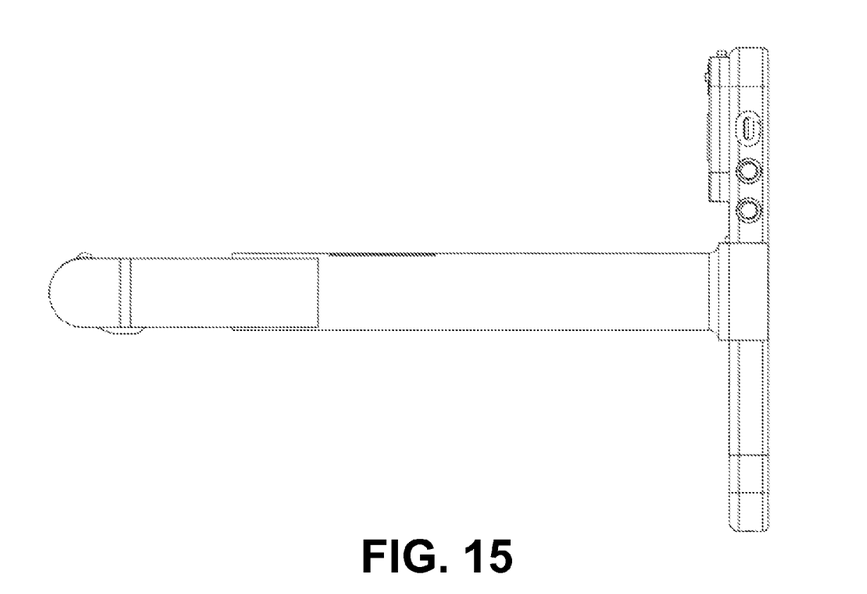

Lens mount 120 is sized to accommodate an ophthalmoscopy lens (not shown) in the range of 10D to 60D, such as a 14D, 20D, 22D, 28D, 30D, 40D, or 54D condensing lens for indirect ophthalmoscopy. The working distance between lens mount 120 and the mobile imaging device is about 5.75" in the case of an iPhone couple to a Volk Panretinal 2.2 lens, but will vary depending on the combination of mobile device and ophthalmoscopy lens power. Ophthalmoscopy lens can be easily mounted and removed from the inner diameter 124 of lens mount 120. In a preferred embodiment, inner diameter 124 of lens mount 120 has a slightly undersized fit to allow gripping of the ophthalmoscopy lens for easy insertion and removal. In another preferred embodiment, opening 126 would be desirable to make the ring of lens mount 120 more flexible to allow easy insertion and removal of the ophthalmoscopy lens. Another design objective of opening 126 relates to minimizing space for the ophthalmoscopy lens adapter 100. It could be desirable that the lens mount 120 can be folded to be parallel and flush with the telescoping arm 110 to minimize space (see FIGS. 14-15). In other embodiments, a clamp mechanism can be used to hold the lens. The clamp could utilize a ratchet type mechanism, a spring mechanism, an adjustable belt, a vice, an elastic band, or screws that can be adjusted to hold the lens in place. In one example, it could be desirable that the ophthalmoscopy lens adapter 100 be minimized in size so that it can be stored in a pocket of a garment, e.g. a pocket of a doctor's coat. Regarding weight, the ophthalmoscopy lens adapter 100, without holding the ophthalmoscopy lens, is preferably less than 100 grams (e.g. made from a polymer or a lightweight metal, such as aluminum) and can be manufactured with any type of process including injection molding and various 3D printing processes.

At end 114' a mobile imaging device mount 130 is attached to which a mobile imaging device can be removably held. In a preferred embodiment, the inner spacing 130' of the mobile imaging device mount has a slightly undersized fit to allow gripping or snap fitting to the mobile imaging device or casing of the mobile imaging device for easy attachment and de-attachment. The mobile imaging device mount could be adjustable to accommodate any sized phone or casing, either through an elastic mechanism, a spring mechanism, an adjustable belt-type mechanism, a vise mechanism, or other type of mechanism that would allow the mount to grip the phone and hold it in position.

Further to the importance in the design and minimization of space of the ophthalmoscopy lens adapter 100 is the structural aspect of an un-encased optical pathway between the mobile imaging device mount 130 and the ophthalmoscopy lens mounted in lens mount 120. In addition, the ophthalmoscopy lens adapter 100 of this invention does not need or have any reflective mirrors.

In another embodiment, the adapter could also include a spacer element that protrudes from the shaft on the ophthalmoscopy lens side that either can rest on the patient's face (such as on the cheek under the eye) or can rest on the user's thumb while the index finder is used to hold the patient's eyelid open. The spacer element may be straight, curved, contain a ring element that can fit around the user's thumb, and/or contain a padding element that rests on the patient's face. The spacer element may also be adjustable in length and be telescoped back into the adapter's main shaft or be folded back on to the adapter's main shaft.

Anterior Segment Adapter Module

A second adapter module (FIG. 2) is a macro lens adapter 200, which can be used for imaging the anterior segment of the eye. The macro lens adapter has a mount for a macro lens 210 capable of showing a close up, focused, magnified view of patient's anterior eye structures. The macro lens is either completely removable or can be reversibly positioned in front of the mobile device camera lens through either a sliding, magnetic, or hinge mechanism. The macro lens may be a commercially available macro lens manufactured specifically for smartphones. In this example, macro lens 210 distinguishes a holding area 212 and a lens area 214. Macro lens 210 can easily be inserted or removed from open slot area 220 of the macro lens adapter 200. Open slot area 220 is sized such that when the macro lens 210 has been slit into open slot area 220 a user will be able to view the lens area 214 of macro lens 210 through opening 222. The macro lens adapter 200 further distinguishes a light source 230, with an on/off switch 240, to focus light onto an eye. Preferably, the light source 230 is an LED light source with an adjustable intensity that can be adjusted with, for example, dial control 250. The control element for the LED intensity may be a dial, but could also be, but not limited to, a knob, a sliding switch, a haptic touch button, or a button. Macro lens adapter 200 can be adapted to the mobile imaging device by using any type of attaching means such as Velcro, a snap fit mechanism, a slide-and-hold mechanism or the like. For this adapter the back area (facing into the figure) is adapted to the mobile imaging device.

Figure 3:
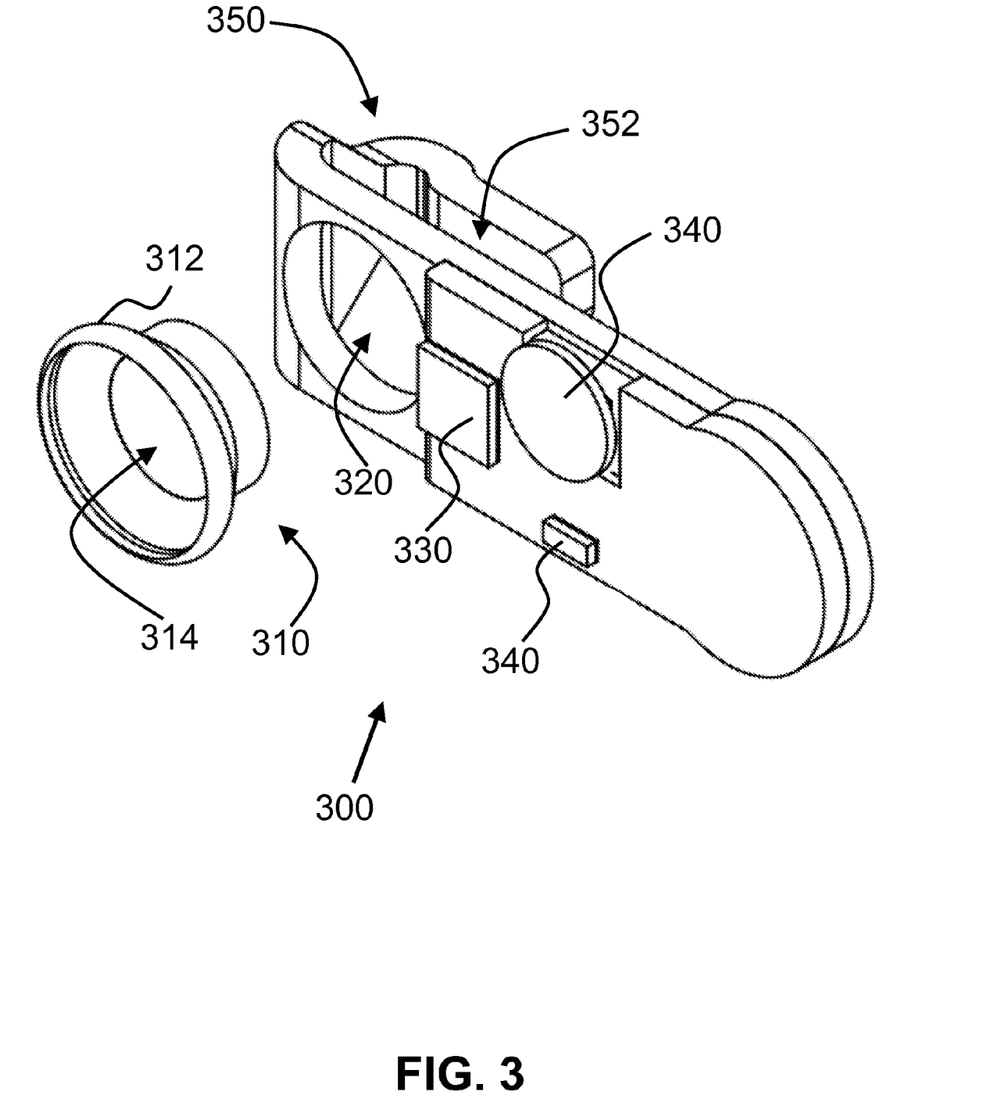

FIG. 3 shows another embodiment of the second adapter module. Macro lens adapter 300 has a macro lens 310. In this example, macro lens distinguishes a holding area 312 and a lens area 314. Macro lens 310 can easily be inserted or removed from open slot area 320 of the macro lens adapter 300. In this example, macro lens 310 can be a single-focus lens or a manually adjustable focus lens where hold area 312 can be used for manual focusing. Open slot area 320 is sized such that when the macro lens 310 has been placed into open slot area 320 a user will be able to view through the lens area 314 of macro lens 310. The macro lens adapter 300 further distinguishes a light source 330, with an on/off switch 340, to focus light onto an eye. Preferably, the light source 330 is an LED light source with an adjustable intensity that can be adjusted with for example dial control 350. Macro lens adapter 300 has a bracket 350 with a space 352 which is defined to fit the width of an area of a mobile imaging device so that the macro lens adapter 300 can either be slit onto (when bracket 350 has no joint mechanism) or clipped onto (when bracket 350 does have a joint or spring mechanism) the mobile imaging device. For this adapter the back area (facing into the figure) is adapted to the mobile imaging device.

In another embodiment, the macro lens can be fixed within a wider slot and able to slide onto and off of the front of the mobile device camera lens. In yet another embodiment, the macro lens can be magnetically attached to the front of the adapter and can slide onto and off of the front of the mobile device camera lens. In still another embodiment, the macro lens can be hinged to the front of the adapter and can be positioned via the hinge onto and off of the front of the mobile device camera lens. The macro lens may have a focal length ranging from about 1 cm to about 20 cm.

Iridocorneal Angle Segment Adapter

Figure 2:
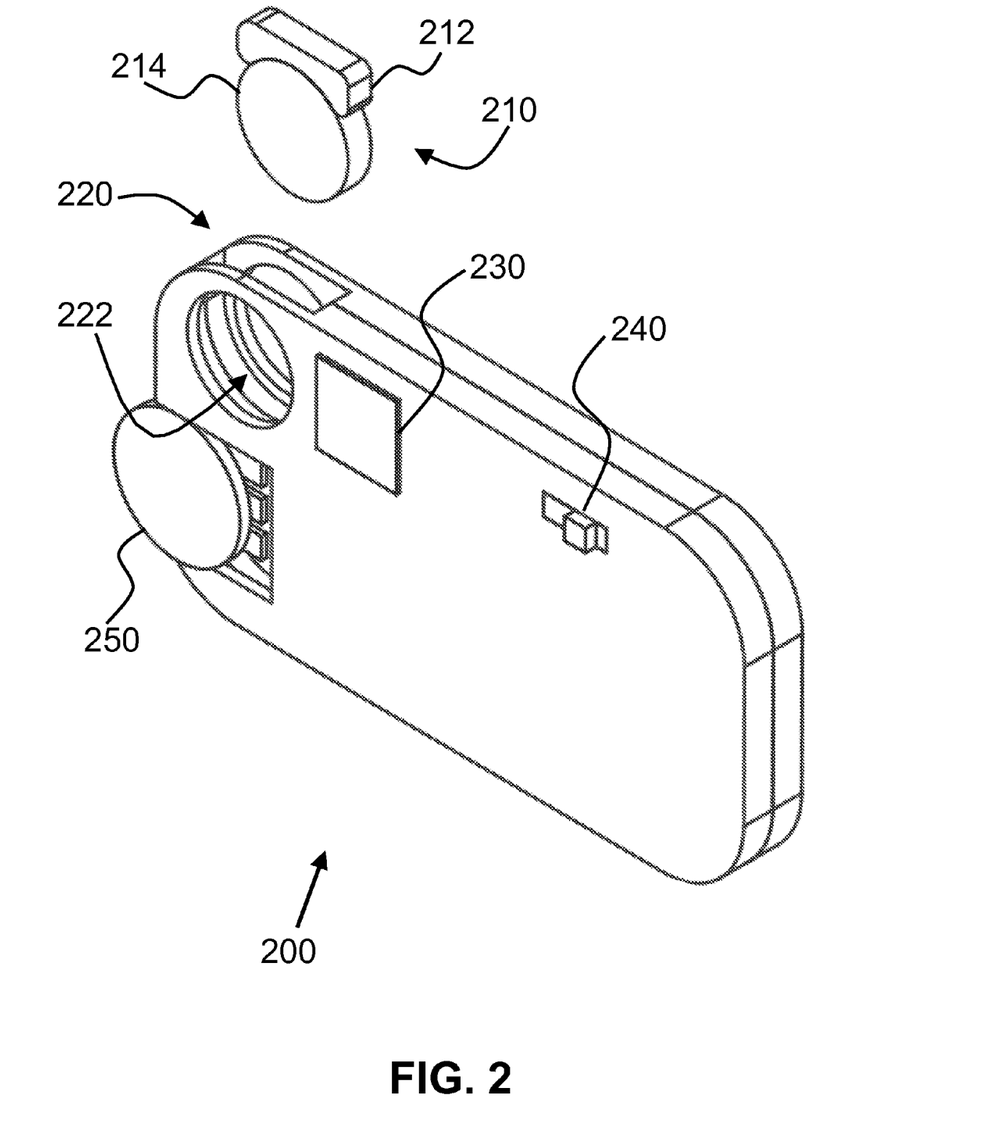
FIGS. 2-3 show macro lens adapters 200, 300 according to exemplary embodiments of the invention.

A third adapter module is a gonioscopy lens adapter for imaging the iridocorneal angle of the eye. The gonioscopy lens adapter is able to hold a gonioscopy lens such as, but not limited, to a Goldmann 3-mirror lens, a Sussman gonioscopy lens, a Posner gonioscopy lens, or a Koeppe lens and could be a single focus lens or an adjustable focus lens. The gonioscopy lens adapter is similar to the macro lens adapters 200, 300 where instead of using a macro lens a gonioscopy lens can be used, but is positioned in such a way that the illumination from the LED light source passes through the lens, and the gonioscopy lens makes contact with patients eyes to eliminate total internal reflection, which is a principle that is known in the art of gonioscopy.

Variable Light Source

A fourth adapter module is a variable intensity light source. In one embodiment, the variable intensity light source is an external variable intensity LED, which can be removably adapted to the mobile imaging device as shown in FIGS. 2-3. With respect to the use of ophthalmoscopy lens adapter 100, the light source of macro lens adapter 200, 300 can be used for application of the ophthalmoscopy lens adapter 100. When both adapters 100 and 200/300 are used in conjunction, the macro lens or gonioscopy lens for adapters 200/300 can be removed so that these lenses would not interfere with the posterior segment analysis of the eye. However, absent of adapters 200/300 either the ophthalmoscopy lens adapter 100 could (i) have its own built-in variable light source for example of the mobile imaging device mount (not shown), or (ii) use a variable light source built-in to the mobile imaging device or operable via an application running on the device in connection with e.g. a flash. Key to the use of the ophthalmoscopy lens adapter 100 is the fact that the variable intensity light source can be coaxially aligned with the ophthalmoscopy lens and the lens of the mobile imaging device. Key to the use of the macro lens adapters 200/300 is the fact that the variable intensity light source can be coaxially aligned with the macro lens or gonioscopy lens.

Ophthalmoscopy System or Kit Modularity

Figure 4:
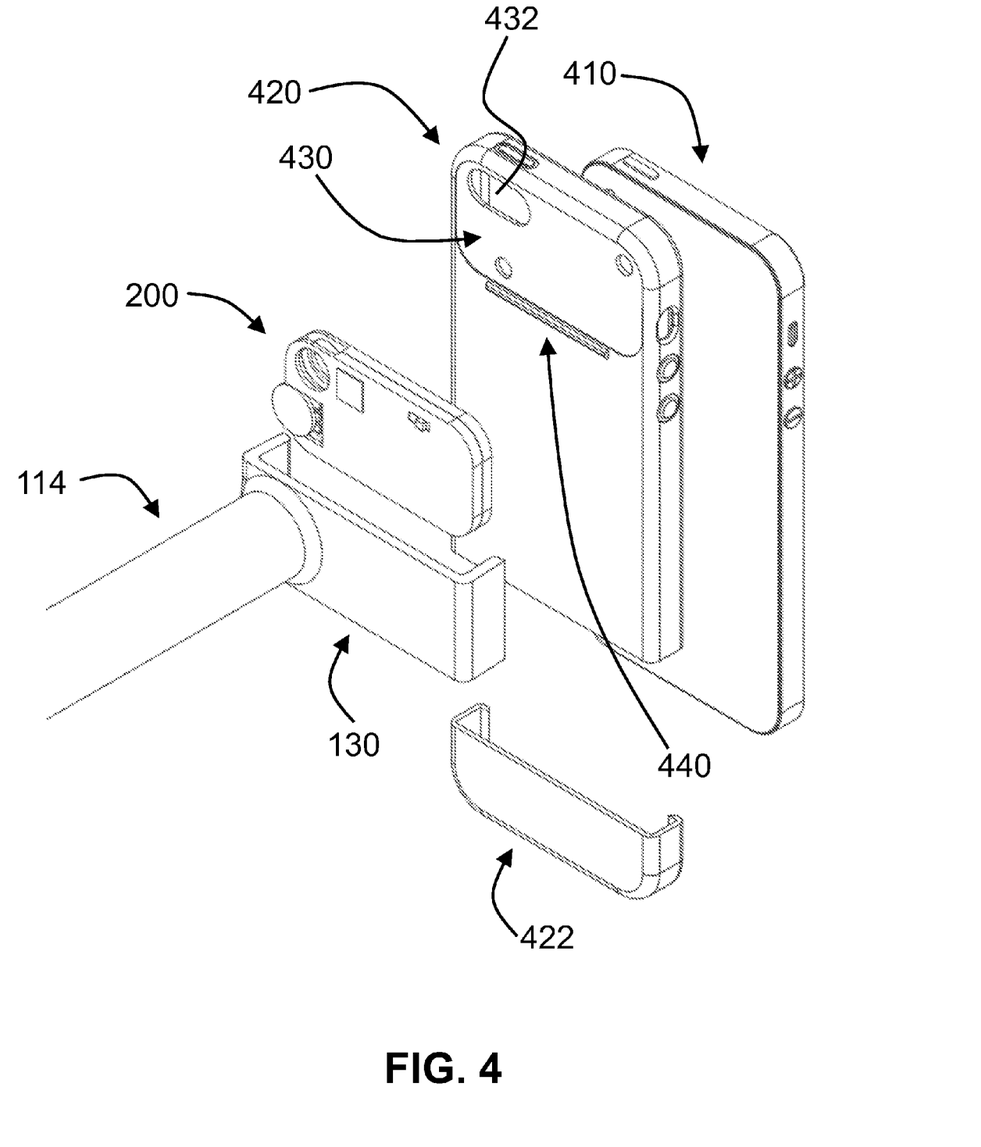
FIG. 4 shows part of ophthalmoscopy lens adapter 100 with macro lens adapter 200.

FIG. 4 shows an exploded view how the ophthalmoscopy lens adapter and the macro lens adapter 200 can be adapted to a mobile imaging device 410 (here portrayed as an iPhone). In this example, a casing can be used that would allow both adapters to be easily connected. Casing could have two parts, 420, 422 that could be snap fit onto mobile imaging device 410 or to each other. Parts 420, 422 could fully enclose the mobile imaging device 410 yet allowing for an opening for the screen/button area of the mobile imaging device 410, or partially enclose where there is at least no enclosing part for the screen/button area of the mobile imaging device 410. Part 420 distinguishes an area 430 to which the macro lens adapter 200 can be placed/positioned. Part 420 also features an opening 432 that lines up lens of the mobile imaging device 410 and the macro lens mounted in open slot area 220. Preferably, the macro lens fits as close as possible to the lens of the mobile imaging device. In addition, the macro lens should be coaxially aligned with the lens of the mobile imaging device. A ridge 440 is featured on part 420 and serves as a guide to place mobile imaging lens mount 130 onto part 420, which allows for proper coaxially alignment of the ophthalmoscopy lens with the lens of the mobile imaging device.

Figure 5:
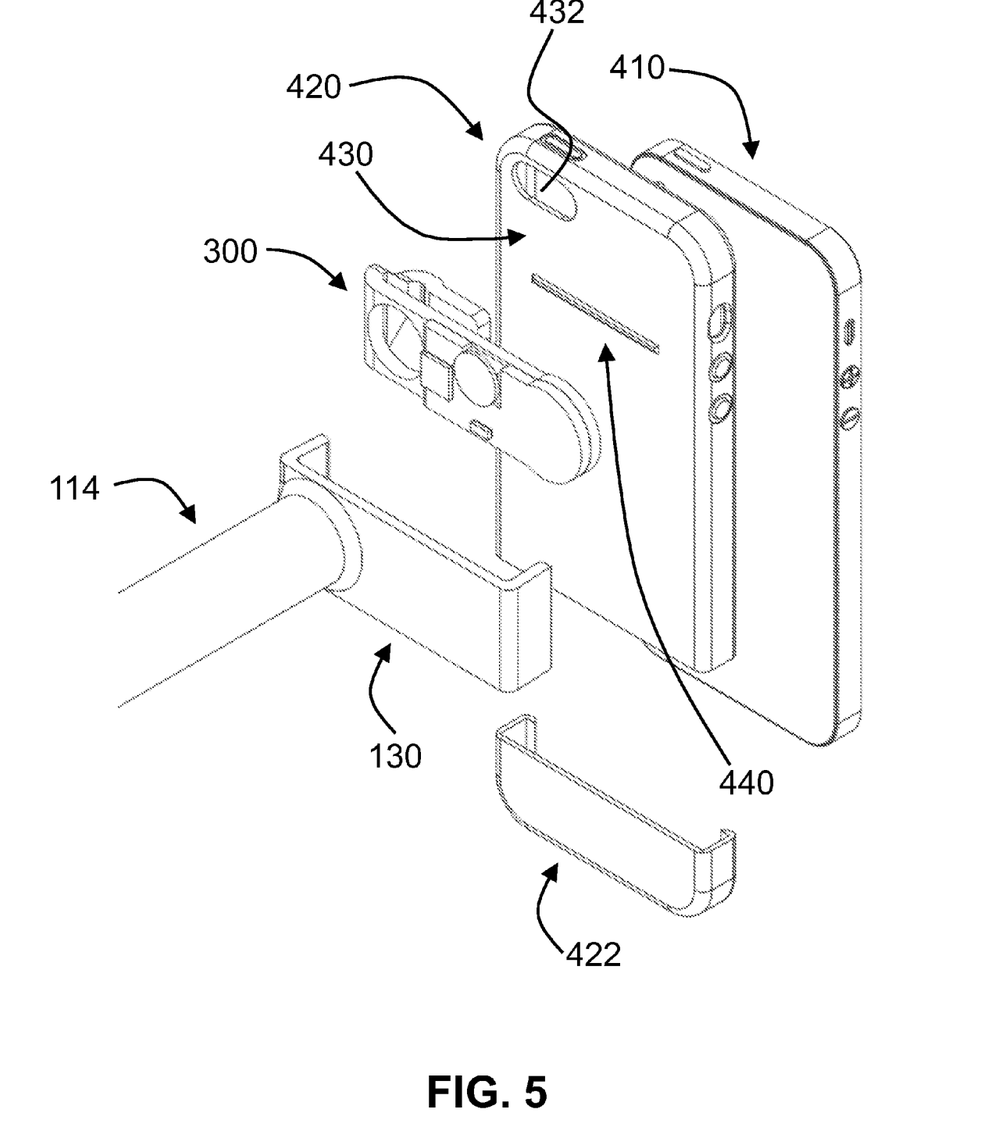
FIG. 5 shows part of ophthalmoscopy lens adapter 100 with macro lens adapter 300.
Figure 6:
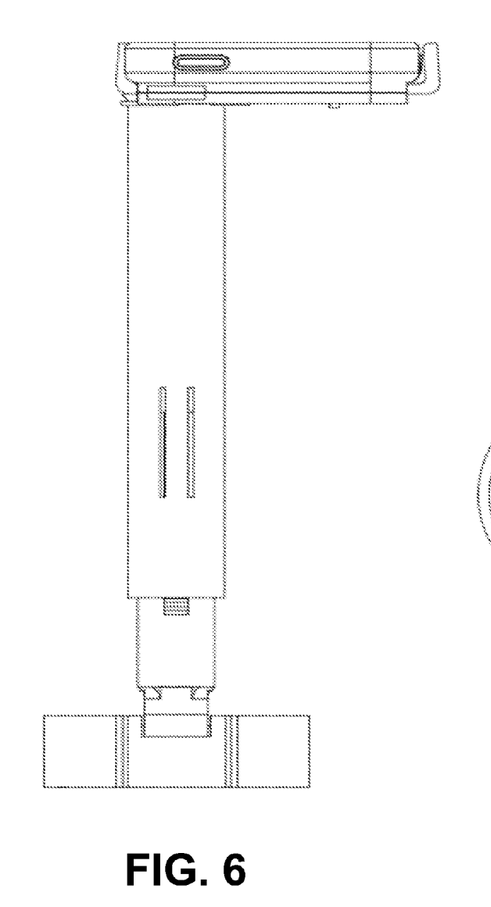
Figure 7:
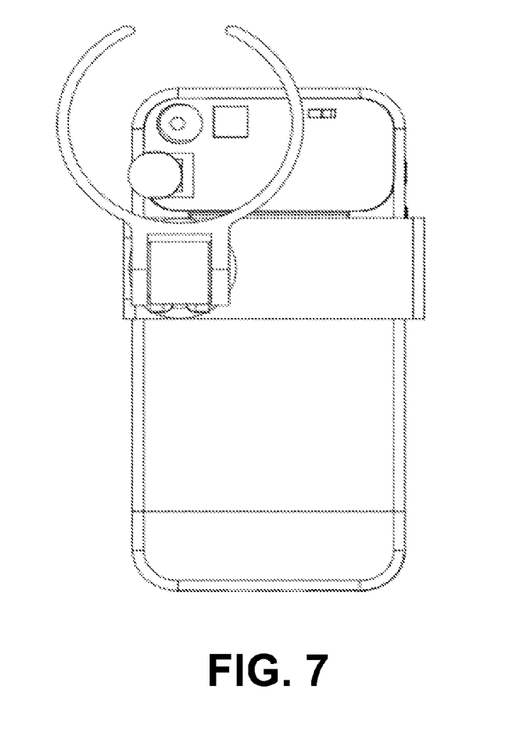
FIG. 7 is a frontal view showing the coaxial alignment of the lenses.
Figure 8:
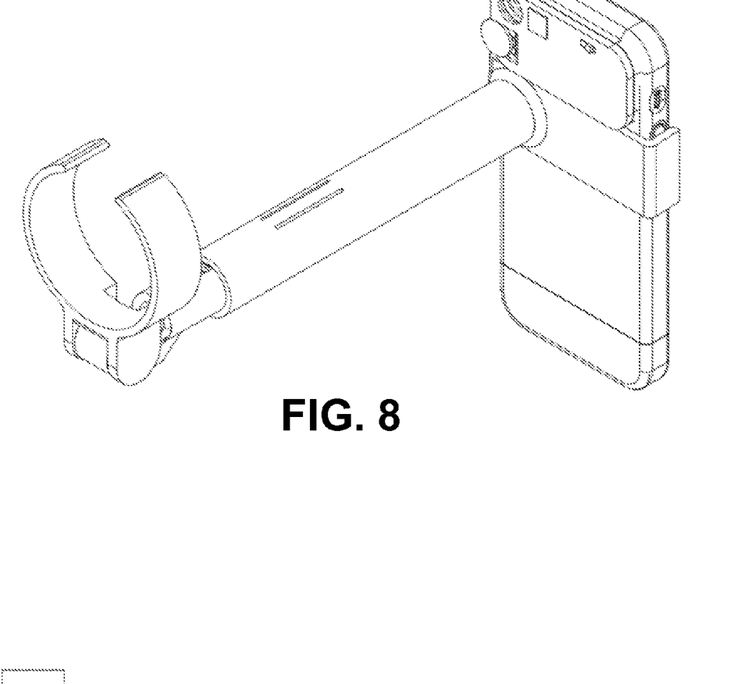
FIG. 8 is a three-dimensional view.
Figure 9:
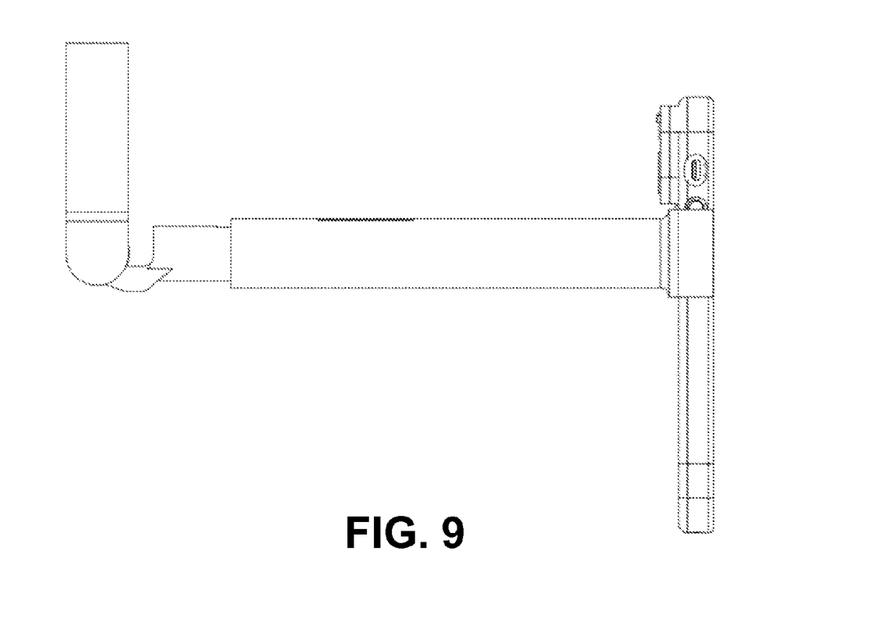
FIG. 9 is a side view.
Figure 10:
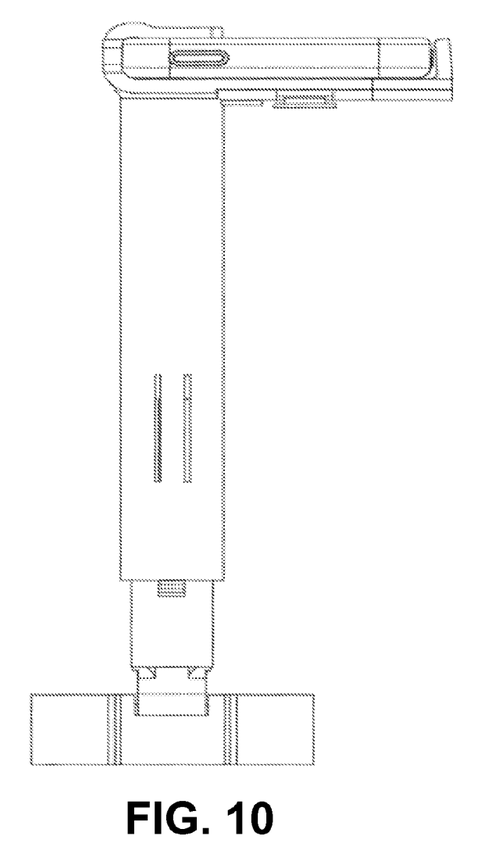
Figure 11:
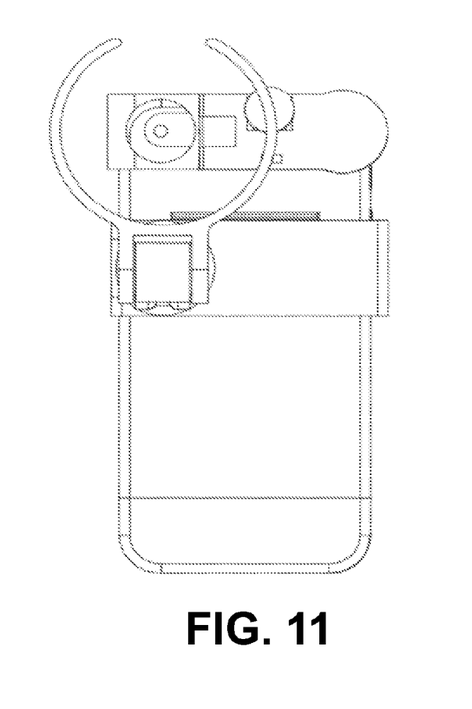
FIG. 11 is a frontal view showing the coaxial alignment of the lenses.
Figure 12:
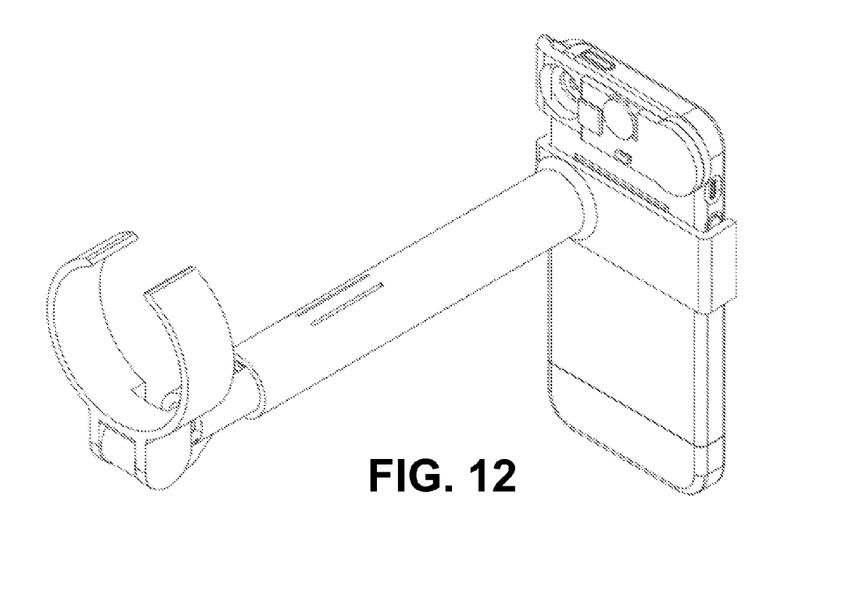
FIG. 12 is a three-dimensional view.
Figure 13:
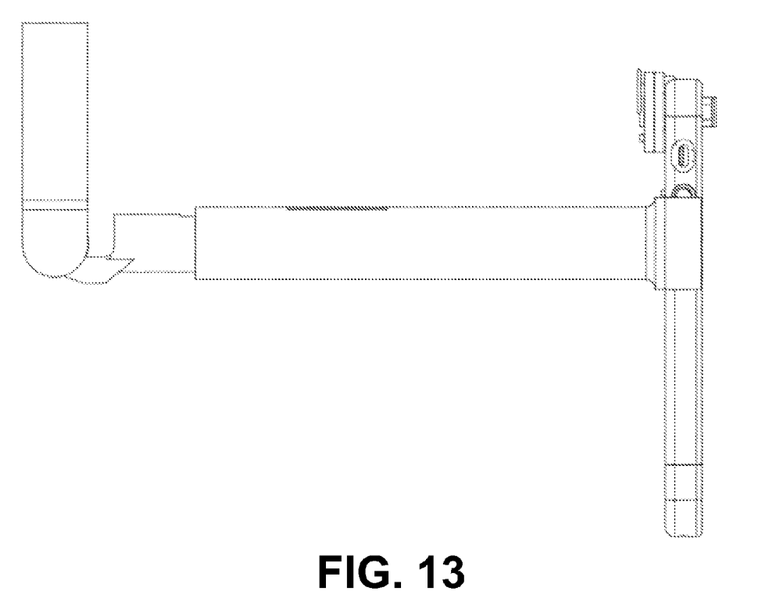
FIG. 13 is a side view.

FIG. 5 shows an exploded view how the ophthalmoscopy lens adapter and the second example of the macro lens adapter 300 can be adapted to a mobile imaging device 410 (here portrayed as an iPhone). Similar to the example in FIG. 4, the macro lens fits as close as possible to the lens of the mobile imaging device. In addition, the macro lens should be coaxially aligned with the lens of the mobile imaging device.

Having a system or kit with the various lens adapter modules, respective lenses and the mobile imaging device, a user is equipped with tools for mobile ophthalmoscopy. The user can setup for various mobile ophthalmoscopy imaging applications:

Posterior segment ophthalmoscopy using the ophthalmoscopy lens adapter with the mobile imaging device and its internal (variable
  Posterior segment ophthalmoscopy using the ophthalmoscopy lens adapter with the mobile imaging device and an external (variable intensity) light source.
  Posterior segment ophthalmoscopy using the ophthalmoscopy lens adapter with the mobile imaging device using the (variable intensity) light source of the macro lens adapter (without the macro lens mounted).

Anterior segment ophthalmoscopy using the macro lens adapter and mounted a macro lens with the mobile imaging device optionally using the (variable intensity) light source of the macro lens adapter, where the ophthalmoscopy lens adapter is detached from the mobile imaging device.

Anterior segment ophthalmoscopy using the macro lens adapter and mounted a macro lens with the mobile imaging device and its internal (variable intensity) light source, where the ophthalmoscopy lens adapter is detached from the mobile imaging device.

Iridocorneal angle ophthalmoscopy (gonioscopy) using a modified macro lens adapter that allows mounting of a gonioscopy lens with the mobile imaging device optionally using the (variable intensity) light source of the macro lens adapter or the mobile device's internal flash.

Variations

The position of the lens mount of the ophthalmoscopy lens adapter should always coaxially aligned with the lens of the mobile imaging device. However, the telescopic arm (or equivalent mechanism) does not have to be mounted as shown in the figures since the mobile imaging device mount could take various shapes and be adapted at various locations with respect to the mobile imaging device.

The telescoping arm can be permanently or reversibly mounted to the mobile device case. In either case, the telescoping arm may be foldable such that the arm and lens mount distal to it are moved aside to allow the user to hold the mobile device closer to the patient's eye when using, for example, the macro lens adapter. The telescoping arm may be attached to the case of the phone either through a two-point fixation undersized gripping mechanism as shown in the drawings, or through other mechanisms such as a depression within the case that fits the telescoping arm (female-male connectivity), a reversible locking fit wherein a button is pressed to release the arm from the case, a magnetic attachment mechanism, or a suction attachment mechanism.

The aperture of the LED light source could be adjustable to create varying diameters for the collimated beam. Blue, red-free, and other types of lighting may be used, and infrared lighting may also be used. In addition, various filters could be used for the light source, for instance, to physically reduce the intensity of the light. This method could be used in place of the variable intensity light source, to provide one or more barrier-type filters for the light. Examples of such filters are neutral density filters and polarizing filters.

In addition, certain elements may be positioned in front of the camera lens to enhance image quality. Such elements include, for example, additional lenses that will serve to increase the magnification of the virtual image created by the ophthalmoscopy lens seen on the mobile imaging device screen (e.g. to enable to occupy a greater percentage of the screen area) as well as filtering elements such as polarizing filters, neutral density filters, and pinhole filters that can reduce glare and light scatter.

The macro lens could be a rotating or sliding macro lens set where user could select from macro, blue filter, high magnification and wide angle lenses by rotation the lens set in front of the lens of the mobile imaging device (not shown).

The macro lens adapter could further include an eye rest, e.g. a circular protrusion around the macro lens which could be place around the eye, to assist in positioning and stabilizing the macro lens adapter and mobile imaging device system and its various modular forms in front of the eye.

The variable intensity external light source could be used with or without a mirror system or fiber optic element to guide the light.

The battery or batteries for the light source may be enclosed within the telescopic shaft, which would have a dual effect of favorably weighting the device toward the side of the phone and also hiding away additional bulk on the device.

The external light source and macro lens adapter component can be attachable to the phone either through a clip mechanism or a plate-attachment mechanism to a case. A magnetic mechanism may also be used that attaches these components either directly to the phone or to the case on the phone.

In all cases, the phone may be attached directly to the components of the kit or in part through a case, which can be positioned around the phone either through a slider-case configuration (as shown in the figures) or a grip-fit configuration wherein the material of the case is flexible enough to surround the phone.

An external fixation target could be added for the opposite eye that can be a blinking light or other form of adjustable fixation target. A moveable extension with a blinking light tip could be plugged into a phone audio jack or directly to the adapter itself (such as to the telescoping shaft or another part of either the anterior or posterior adapter) to direct a patient's gaze toward the light.

The LED light could be focused into an adjustable slit beam that can be directed through the cornea at an angle, mimicking the action of a traditional slit lamp. The LED light may also be set to a fixed intensity (without a variable intensity function).

The system could be enhanced to have a dedicated software application running on the mobile imaging device to assist in image capture, light control, image analysis, image enhancement, data storage and data sharing as are common features of applications running on, for example, smartphones.

What is claimed is:

1. A modular lens adapter system for mobile anterior and posterior segment ophthalmoscopy, comprising:
   (a) a variable intensity light source;
   (b) an ophthalmoscopy lens adapter for imaging the posterior segment of an eye,
       wherein the ophthalmoscopy lens adapter comprises a telescoping arm with two ends, wherein on the one end the telescoping arm comprises a lens mount configured to removably mount an ophthalmoscopy lens, and wherein on the other end the telescoping arm comprises a mobile imaging device mount configured to removably mount a mobile imaging device,
       wherein the telescoping arm can be oriented to position the ophthalmoscopy lens at various distances with respect to the lens of the mobile imaging device,
       wherein the ophthalmoscopy lens is configured to be coaxially aligned with the lens of the mobile imaging device, and
       wherein the variable intensity light source is configured to be coaxially aligned with the ophthalmoscopy lens and the lens of the mobile imaging device; and
   (c) a macro lens adapter comprising a lens mount configured to removably mount a macro lens for imaging the anterior segment of the eye, wherein the macro lens adapter is configured to be removably adapted to the mobile imaging device, wherein the variable intensity light source is configured to be coaxially aligned with the macro lens, and wherein the macro lens is configured to be coaxially aligned with the lens of the mobile imaging device.

2. The system as set forth in claim 1, wherein the ophthalmoscopy lens adapter has an un-encased optical pathway between the mobile imaging device mount and the ophthalmoscopy lens.

3. The system as set forth in claim 1, wherein the ophthalmoscopy lens adapter does not have reflective mirrors.

4. The system as set forth in claim 1, wherein the variable intensity light source and the macro lens adapter are integrated as one adapter configured.

5. The system as set forth in claim 1, wherein the variable intensity light source is an external variable intensity LED adapter, configured to be removably adapted to the mobile imaging device.

6. The system as set forth in claim 1, wherein the variable intensity light source is a variable intensity LED built-in to the mobile imaging device.

7. The system as set forth in claim 1, wherein the telescoping arm can position the lens mount from the mobile phone mount in a range of 1 cm to 20 cm.

8. The system as set forth in claim 1, wherein the ophthalmoscopy lens adapter, without holding the ophthalmoscopy lens, is less than 100 grams.

9. The system as set forth in claim 1, wherein the lens mount of the macro lens adapter is configured to fit as close as possible to the lens of the mobile imaging device.

10. The system as set forth in claim 1, wherein the lens mount of the ophthalmoscopy lens adapter can be folded to be parallel and flush with the telescoping arm to minimize space.

11. The system as set forth in claim 1, wherein the ophthalmoscopy lens adapter can be minimized in size so that it can be stored in a pocket of a garment.

12. The system as set forth in claim 1, further comprising a gonioscopy lens adapter having a lens mount configured to removably mount a gonioscopy lens for imaging the iridocorneal angle of the eye, wherein the gonioscopy lens adapter is configured to be removably adapted to the mobile imaging device, wherein the variable intensity light source is configured to be coaxially aligned with the gonioscopy lens, and wherein the gonioscopy lens adapter is configured to be coaxially aligned with the lens of the mobile imaging device.

13. The system as set forth in claim 1, wherein the macro lens adapter is configured to mount a gonioscopy lens for imaging the iridocorneal angle of the eye.

* * * * *